(12) United States Patent
Zhang et al.

(10) Patent No.: US 9,403,853 B2
(45) Date of Patent: *Aug. 2, 2016

(54) TRIMETHYLOLPROPANE CORE, PHOSPHONIC ACID TERMINATED DENDRIMER AND ITS PREPARATION METHOD

(71) Applicant: Tongji University, Shanghai (CN)

(72) Inventors: Bingru Zhang, Shaghai (CN); Fengting Li, Shanghai (CN); Hongmei You, Shanghai (CN)

(73) Assignee: Tongji University, Shanghai (CN)

( * ) Notice: Subject to any disclaimer, the term of this patent is extended or adjusted under 35 U.S.C. 154(b) by 346 days.

This patent is subject to a terminal disclaimer.

(21) Appl. No.: 14/022,145

(22) Filed: Sep. 9, 2013

(65) Prior Publication Data

US 2014/0332470 A1  Nov. 13, 2014

(30) Foreign Application Priority Data

May 7, 2013  (CN) .......................... 2013 1 0165806

(51) Int. Cl.

| | |
|---|---|
| C07F 9/22 | (2006.01) |
| C07F 9/28 | (2006.01) |
| C02F 5/12 | (2006.01) |
| C02F 5/14 | (2006.01) |
| B01D 65/02 | (2006.01) |
| B01D 65/08 | (2006.01) |
| C07F 9/38 | (2006.01) |
| C07F 9/40 | (2006.01) |
| C02F 1/00 | (2006.01) |
| C02F 5/10 | (2006.01) |
| C02F 1/44 | (2006.01) |
| C02F 103/02 | (2006.01) |
| C02F 103/10 | (2006.01) |

(52) U.S. Cl.
CPC .............. *C07F 9/3817* (2013.01); *B01D 65/08* (2013.01); *C02F 5/14* (2013.01); *C07F 9/3843* (2013.01); *C07F 9/4009* (2013.01); *B01D 2321/16* (2013.01); *B01D 2321/168* (2013.01); *C02F 2103/023* (2013.01); *C02F 2103/10* (2013.01); *C02F 2303/22* (2013.01); *C07F 9/3847* (2013.01)

(58) Field of Classification Search
None
See application file for complete search history.

(56) References Cited

U.S. PATENT DOCUMENTS

| 4,758,635 A * | 7/1988 | Wilson | B01J 45/00 525/418 |
|---|---|---|---|
| 5,358,642 A * | 10/1994 | Chen | C02F 5/14 210/700 |
| 2006/0021938 A1 * | 2/2006 | Diallo | B01D 61/04 210/638 |
| 2013/0256593 A1 * | 10/2013 | Herfert | B01J 20/267 252/194 |

FOREIGN PATENT DOCUMENTS

WO  WO2013148911 A1 * 10/2013 ................ C02F 5/14

* cited by examiner

*Primary Examiner* — Joseph Drodge
*Assistant Examiner* — Clare Perrin

(57) ABSTRACT

A trimethylolpropane core, phosphonic acid terminated dendrimer and its preparation method are provided, And a preparation method thereof comprises steps of processing Michael addition reaction on trimethylolpropane triacrylate ($CH_3CH_2C(CH_2OCOCH_2=CH_2)_3$) and alkylidene diamine ($NH_2CH_2(CH_2)_nNH_2$), wherein n is an integer from 1 to 5, so as to obtain trimethylolpropane core, amino group terminated dendrimer, and modifying the amino group by methylene phosphonic acid to obtain the trimethylolpropane core, phosphonic acid terminated dendrimer having a chemical formula of $CH_3CH_2C[CH_2OCOCH_2CH_2N(CH_2PO_3H_2)CH_2(CH_2)_nN(CH_2PO_3H_2)_2]_3$, wherein n is an integer from 1 to 5. The trimethylolpropane core, phosphonic acid terminated dendrimer has high calcium tolerance, and excellent inhibiting efficiency of calcium carbonate, calcium sulfate and barium sulfate, which is applied in inhibiting the formation and deposition in industrial water systems of circulating cooling water, oilfield flooding and reverse osmosis, and particularly suitable for water treatment with high calcium tolerance.

7 Claims, No Drawings

TRIMETHYLOLPROPANE CORE, PHOSPHONIC ACID TERMINATED DENDRIMER AND ITS PREPARATION METHOD

BACKGROUND OF THE PRESENT INVENTION

1. Field of Invention

The present invention relates to the technical field of water treatment to inhibit the formation of scales. More particularly, the present invention relates to a process for producing trimethylolpropane core, phosphonic acid terminated dendrimer and methods of inhibiting scales formation in industrial water systems, such as boiler, cooling, desalination, and oil production, especially in the industrial water treatment under the condition of high calcium concentration.

2. Description of Related Arts

Nowadays, water shortage and serious water pollution have become worldwide problems. Improving technical levels of industrial water treatment such as circulating cooling water, oilfield flooding and reverse osmosis has become an important measure for energy saving and emission reduction.

Industrial water accounts for a proportion of over two thirds of city water consumption, and the circulating cooling water accounts for 70~85% of the industrial water. Therefore, increasing cycles of concentration of industrial circulating cooling water has become an effective treasure for conservation and protection of water resources. However, with the increase of the cycles of concentration in the circulating cooling water and calcium concentration, advanced requirement is put forward to antisclants used for the circulating cooling water treatment, i.e., antiscalants should not only be capable of inhibiting scales but also have high calcium tolerance simultaneously.

With the increasing scarcity of freshwater resources, reverse osmosis water treatment, which is simple, efficient and economical, is increasingly applied to fields such as desalination of seawater and brackish water, preparation of ultrapure water and wastewater treatment, and has become the first selected technology and technical support for promoting virtuous cycle of water resource utilization. However, with the increase of reverse osmosis recovery ratio, the calcium concentration on the reject side of the membrane is gradually increasing, and especially in seawater or brackish water, the calcium concentration is higher, which requires the antiscalants to have excellent inhibiting scale performance under high calcium concentration, i.e., the antiscalants should have higher calcium tolerance.

There are two series in the conventional scale inhibition and dispersion agent, phosphonates and carboxylate polymers. For having good efficiency of corrosion and scale inhibition, phosphonates has been widely applied. Besides 1-Hydroxyethylidene-1,1-diphosphonic (HEDP) and 2-phosphonobutane-1,2,4-tricarboxylic acid (PBTCA), the phosphonates currently available on the market mainly belongs to amino methylene phosphonic acid, such as amino trimethylene phosphonic acid (ATMP), ethylene diamine tetra(methylenephosphonic acid) (EDTMP), diethylenetriamine penta(methylenephosphonic acid) (DTPMP), hexamethylene diamine tetra(methylene phosphonic acid) (HDTMP) and polyamino polyether tetra(methylene phosphonate) (PAPEMP).

Except that the PAPEMP is oligomer, the phosphonates based methylene phosphonic acid mentioned all belong to micromolecular compounds. Due to low price and good scale inhibition efficiency thereof, the phosphonates of micromolecular methylene phosphonic acid is widely applied to industrial water treatment, and occupies a great market share therein. However, almost all of the micromolecular phosphonates has no satisfying calcium tolerance.

Compared with other micromolecular phosphonates based methylene phosphonic acid such as ATMP, EDTMP, DTPMP and HTDMP, PAPEMP belongs to polymer and has a higher molecular weight. U.S. Pat. Nos. 5,535,157 and 5,358,642 disclose that PAPEMP has high calcium tolerance and is suitable for harsh conditions of high hardness water. However, PAPEMP has far less inhibition scale efficiency than micromolecular phosphonates under conditions of low calcium concentration, and requires a higher concentration of antiscalants for the same inhibition scale effect. Meanwhile, PAPEMP has bad scale inhibition efficiency to barium sulfate and is not suitable for scale inhibition treatment on oilfield flooding and reverse osmosis water.

Compared with linear polymers, dendrimer, which is a new type polymer in recent years, has structural characteristics of accurate molecular structure, high geometric symmetry, a great quantity of functional groups in periphery, cavity existed in the molecule, controllability of molecular weight and nanometer-sized molecule and etc. Therefore, the dendrimer draws universal concern of more and more scientists from all over the world and has important application prospects in many areas such as industry, agriculture, national defense, biomedicine, delivery material and catalysis.

The trimethylolpropane core, phosphonic acid terminated dendrimer prepared by the present invention are new structure, and not disclosed both in China and other countries. Experimental results show that the new type dendrimer has high calcium tolerance, and excellent inhibiting scale performances for calcium carbonate, calcium sulfate and barium sulfate.

SUMMARY OF THE PRESENT INVENTION

An object of the present invention is to provide a high calcium tolerance, trimethylolpropane core, phosphonic acid terminated dendrimer and its preparation method.

Accordingly, in order to accomplish the object mentioned above, the present invention provides a new type dendrimer having methylene phosphonic acid, i.e., a trimethylolpropane core, phosphonic acid terminated dendrimer, which has the following structure formula of:

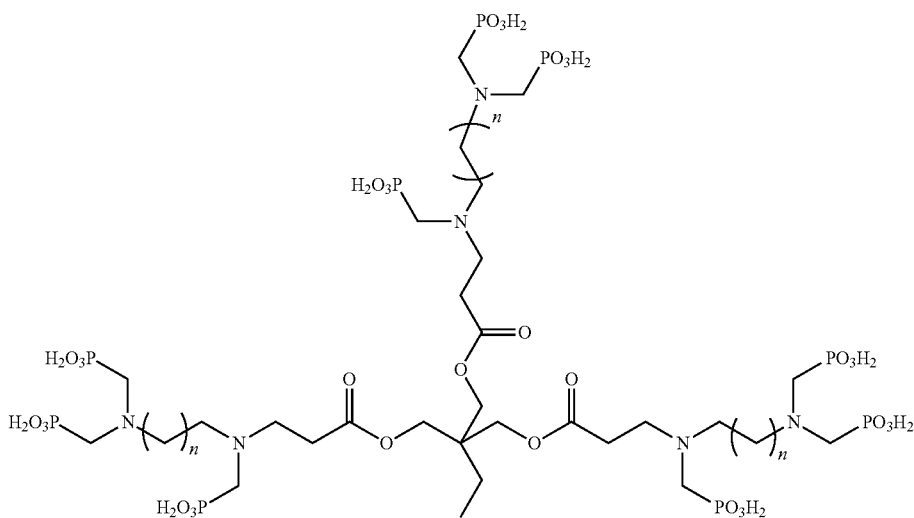

wherein n is an integer from 1 to 5.

The present invention provides a method for preparing the trimethylolpropane core, phosphonic acid terminated dendrimer, which comprises concrete steps as follows.

(1) Synthesis of Trimethylolpropane Core, Amino Terminated Dendrimer

The alkylenediamine (ADA for abbreviation) is added into a round-bottom flask equipped with a stirring, a reflux condenser and a thermometer, and cooled to 10° C. below under nitrogen. The methanol solution of trimethylolpropane triacrylate (TMPTA for abbreviation) is then added to the flask, and the mixture is allowed to react at 25~35° C. for 20~48 hours, The result solution is subjected to vacuum distillation to remove excess alkylidenediamine (ADA) and methanol at 60~110° C. for 5~10 hours to obtain a light-amber viscous material, i.e., intermediate trimethylolpropane core, amino terminated dendrimer (TMPTA-ADA-9NH for abbreviation), wherein a general reaction equation thereof is as follows:

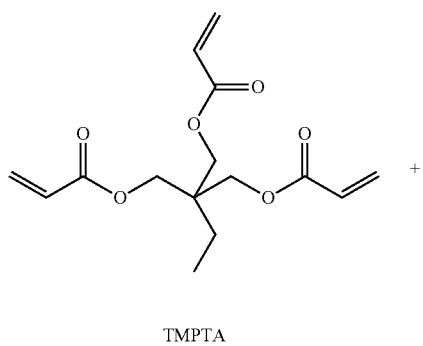

TMPTA

3 H₂N⁀⁀NH₂

ADA

-continued

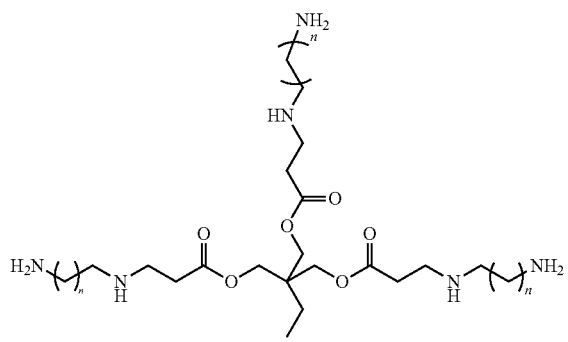

TMPTA-ADA-9NH wherein n is an integer from 1 to 5.

(2) Synthesis of Trimethylolpropane Core, Phosphonic Acid Terminated Dendrimer

Phosphorous acid and concentrated hydrochloric acid are respectively placed in a four-necked flask equipped with a condenser, a stirring, a thermometer and a dropping funnel. Next, aqueous solution of the intermediate trimethylolpropane core, amino terminated dendrimer (TMPTA-ADA-9NH for abbreviation) is slowly added to above mixture solution with cooling and stirring in such a rate to maintain temperature below 40° C. The resulting mixture is heat up to 85~90° C., and formaldehyde solution is then added to the mixture with stirring to form a reaction mixture, the temperature of the reaction mixture maintains at 90° C. for 1~2 hour, and then is elevated to 102~105° C. for a reflux period of 2~4 hours, after the reflux, reaction mixture is concentrated at 102~105° C., and meanwhile, hydrochloric acid is removed off with HCl absorption bottle. Next, the reaction mixture is cooled to ambient temperature, to give an amber transparent liquid product with 30~40% solid content by weight, i.e., the trimethylolpropane core, phosphonic acid terminated dendrimer (TMPTA-ADA-9PO₃H₂), wherein a general reaction equation thereof is as follows:

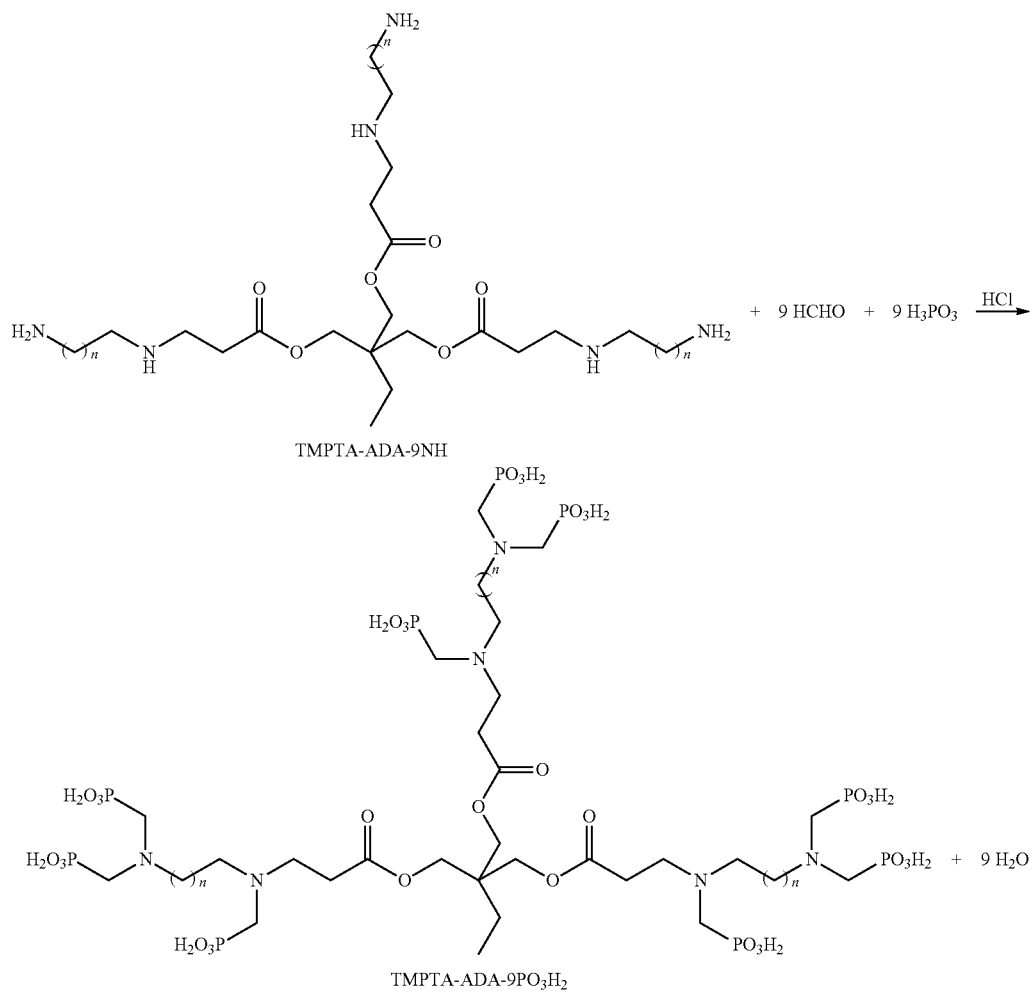

wherein n is an integer from 1 to 5.

In the step (1) of the present invention, a molar ratio of the trimethylolpropane triacrylate to the alkylenediamine is 1:4~6.

In the step (2) of the present invention, a molar ratio of the intermediate trimethylolpropane core, amino terminated dendrimer (TMPTA-ADA-9NH), the phosphorous acid, the formaldehyde and the hydrochloric acid is 1:(9.0~9.2):(11.0~12.0):(11.0~12.0).

In the present invention, the trimethylolpropane triacrylate is provided commercially.

In the present invention, the alkylenediamine is provided commercially, which has a chemical formula of $NH_2CH_2(CH_2)_n-NH_2$, wherein n is an integer from 1 to 5.

In the present invention, the phosphorous acid ($H_3PO_3$) is provided commercially about 99.0% pure.

In the present invention, the formaldehyde (HCHO) is provided commercially about 37% by weight.

In the present invention, the concentrated hydrochloric acid (HCl) is provided commercially about 37% by weight.

The trimethylolpropane core, phosphonic acid terminated dendrimer prepared according to the present invention is a dendrimer having a terminal group of methylene phosphonic acid. Studies show that the trimethylolpropane core, phosphonic acid terminated dendrimer provided by the present invention has a high inhibition scale efficiency under the condition of high concentration calcium due to a special dendrimer structure thereof.

The trimethylolpropane core, phosphonic acid terminated dendrimer provided by the present invention is able to effectively inhibit formation of scales, such as calcium carbonate, calcium sulfate and barium sulfate. The trimethylolpropane core, phosphonic acid terminated dendrimer has a high calcium tolerance, and can be widely used in circulating cooling water system having a high concentration multiple, boiler water, oil field water, sea water desalination, etc.

These and other objectives, features, and advantages of the present invention will become apparent from the following detailed description, the accompanying drawings, and the appended claims.

DETAILED DESCRIPTION OF THE PREFERRED EMBODIMENT

The methylene phosphonic acid antiscalants in the following comparison examples 1~4 are all commercially available.

Comparison example 1: micromolecular phosphonate antiscalant amino trimethylene phosphonic acid (ATMP)

Comparison example 2: micromolecular phosphonate antiscalant ethylene diamine tetra(methylene phosphonic acid) (EDTMP)

Comparison example 3: micromolecular phosphonate antiscalant hexane diamine tetra(methylene phosphonic acid) (HDTMP)

Comparison example 4: macromolecular oligomer phosphonate antiscalant polyamino polyether tetra (methylene phosphonic acid) (PAPEMP)

Example 1

Preparation Method of Trimethylolpropane Core, Phosphonic Acid Terminated Dendrimer 36.00 g of ethylenediamine (EDA) (0.60 mol) was added into a round-bottom flask with a stirring, a reflux condenser and a thermometer, and cooled to 10° C. below under nitrogen. 74.00 g of methanol solution of trimethylolpropane triacrylate (TMPTA) (40%, 0.1 mol) was added to the round-bottom flask, and the mixture is allowed to react at 25° C. for 24 hours. The result solution is subjected to vacuum distillation to remove excess ethylenediamine (EDA) and methanol at 80° C. for 5 hours, to yield 47.61 g of light-amber viscous material, i.e., intermediate trimethylolpropane core, amino terminated dendrimer (TMPTA-EDA-9NH for abbreviation). 37.52 g of phosphorous acid (99.0%, 0.453 mol) and 54.26 g of concentrated hydrochloric acid (37%, 0.550 mol) were respectively placed and uniformly mixed in a four-necked flask equipped with a condenser, a stirring, a thermometer and a dropping funnel. Next, 47.60 g (50%, 0.05 mol) aqueous solution of the intermediate trimethylolpropane core, amino terminated dendrimer (TMPTA-EDA-9NH) was slowly added to above mixture solution with cooling and stirring in such a rate to maintain temperature below 40° C. The resulting mixture was heated up to 85° C., and 44.60 g of formaldehyde solution (37%, 0.550 mol) was then added to the mixture with stirring to form a reaction mixture. The temperature of the reaction mixture maintained at 90° C. for 1 hour, and then was elevated to 103° C. for a reflux period of 4 hours. After the reflux, reaction mixture was concentrated at 103° C. for 1 hour, and meanwhile, hydrochloric acid was removed off with HCl absorption bottle. Next, the reaction mixture was cooled to ambient temperature, to give an amber transparent liquid product with 38.90% solid content by weight, i.e., the trimethylolpropane core, phosphonic acid terminated dendrimer (TMPTA-EDA-9PO$_3$H$_2$).

$^{13}$C NMR (D$_2$O) of TMPTA-EDA-9NH: 6.70; 21.11; 35.61; 38.22; 42.12; 48.06; 50.35; 62.17; 174.87 ppm.

$^{13}$C NMR (D$_2$O) of TMPTA-EDA-9PO$_3$H$_2$: 8.85; 20.96; 33.46; 35.71; 51.67; 52.39; 54.22; 54.86; 56.45; 65.77; 173.21 ppm.

Example 2

Preparation Method of Trimethylolpropane Core, Phosphonic Acid Terminated Dendrimer 44.40 g of 1,3-Propanediamine (PDA) (0.60 mol) was added into a round-bottom flask with a stirring, a reflux condenser and a thermometer, and cooled to 10° C. below under nitrogen. 74.00 g methanol solution of trimethylolpropane triacrylate (TMPTA) (40%, 0.1 mol) was added to the round-bottom flask, and the mixture is allowed to react at 25° C. for 24 hours. The result solution is subjected to vacuum distillation to remove excess 1,3-Propanediamine (PDA) and methanol at 90° C. for 5 hours, to yield 51.83 g of light-amber viscous material, i.e., intermediate trimethylolpropane core, amino terminated dendrimer (TMPTA-PDA-9NH). 37.52 g of phosphorous acid (99.0%, 0.453 mol) and 54.26 g of concentrated hydrochloric acid (37%, 0.550 mol) were respectively placed and uniformly mixed in a four-necked flask equipped with a condenser, a stirring, a thermometer and a dropping funnel. Next, 51.80 g (50%, 0.05 mol) aqueous solution of the intermediate trimethylolpropane core, amino terminated dendrimer (TMPTA-PDA-9NH) was slowly added to above mixture solution with cooling and stirring in such a rate to maintain temperature below 40° C. The resulting mixture was heated up to 85° C., and 44.60 g of formaldehyde solution (37%, 0.550 mol) was then added to the mixture with stirring to form a reaction mixture. The temperature of the reaction mixture maintained at 90° C. for 1 hour, and then was elevated to 105° C. for a reflux period of 4 hours. After the reflux, reaction mixture was concentrated at 105° C. for 1 hour, and meanwhile, hydrochloric acid was removed off with HCl absorption bottle. Next, the reaction mixture was cooled to ambient temperature, to give an amber transparent liquid product with 39.87% solid content by weight, i.e., the trimethylolpropane core, phosphonic acid terminated dendrimer (TMPTA-PDA-9PO$_3$H$_2$).

$^{13}$C NMR (D$_2$O) of TMPTA-PDA-9NH: 6.89; 20.23; 31.05; 35.72; 36.18; 38.55; 43.74; 47.95; 65.78; 172.13 ppm.

$^{13}$C NMR (D$_2$O) of TMPTA-PDA-9PO$_3$H$_2$: 8.02; 21.19; 23.25; 32.76; 34.97; 47.22; 49.23; 50.69; 55.29; 58.44; 62.49; 175.71 ppm.

Example 3

Preparation Method of Trimethylolpropane Core, Phosphonic Acid Terminated Dendrimer 52.80 g of 1,4-Butanediamine (BDA) (0.60 mol) was added into a round-bottom flask with a stirring, a reflux condenser and a thermometer, and cooled to 10° C. below under nitrogen. 74.00 g methanol solution of trimethylolpropane triacrylate (TMPTA) (40%, 0.1 mol) was added to the round-bottom flask, and the mixture is allowed to react at 25° C. for 24 hours. The result solution is subjected to vacuum distillation to remove excess 1,4-Butanediamine (BDA) (0.60 mol) and methanol at 110° C. for 8 hours, to yield 56.06 g of light-amber viscous material, i.e., intermediate trimethylolpropane core, amino terminated dendrimer (TMPTA-BDA-9NH for abbreviation).

37.52 g of phosphorous acid (99.0%, 0.453 mol) and 54.26 g of concentrated hydrochloric acid (37%, 0.550 mol) were respectively placed and uniformly mixed in a four-necked flask equipped with a condenser, a stirring, a thermometer and a dropping funnel. Next, 47.60 g (50%, 0.05 mol) aqueous solution of the intermediate trimethylolpropane core, amino terminated dendrimer (TMPTA-BDA-9NH) was slowly added to above mixture solution with cooling and stirring in such a rate to maintain temperature below 40° C. The resulting mixture was heated up to 85° C., and 44.60 g of formaldehyde solution (37%, 0.550 mol) was then added to the mixture with stirring to form a reaction mixture. The temperature of the reaction mixture maintained at 90° C. for 1 hour, and then was elevated to 105° C. for a reflux period of 4 hours. After the reflux, reaction mixture was concentrated at 105° C. for 1 hour, and meanwhile, hydrochloric acid was removed off with HCl absorption bottle. Next, the reaction mixture was cooled to ambient temperature, to give an amber transparent liquid product with 40.09% solid content by weight, i.e., the trimethylolpropane core, phosphonic acid terminated dendrimer (TMPTA-BDA-9PO$_3$H$_2$).

$^{13}$C NMR (D$_2$O) of TMPTA-BDA-9NH: 7.04; 20.19; 26.22; 28.02; 36.17; 37.54; 44.48; 47.89; 48.93; 66.37; 171.41 ppm.

$^{13}$C NMR (D$_2$O) of TMPTA-BDA-9PO$_3$H$_2$: 8.36; 21.01; 26.34; 26.98; 34.69; 36.55; 52.12; 54.76; 56.08; 59.11; 59.93; 67.27; 174.92 ppm.

Example 4

Preparation Method of Trimethylolpropane Core, Phosphonic Acid Terminated Dendrimer 69.60 g of 1,6-Hexanediamine (HDA) (0.60 mol) was added into a round-bottom flask with a stirring, a reflux condenser and a thermometer, and cooled to 10° C. below under nitrogen. 74.00 g methanol solution of trimethylolpropane triacrylate (TMPTA) (40%, 0.1 mol) was added to the round-bottom flask, and the mixture is allowed to react at 25° C. for 24 hours. The result solution is subjected to vacuum distillation to remove excess 1,6-Hexanediamine (HDA) (0.60 mol) and methanol at 110° C. for 8 hours, to yield 64.46 g of light-amber viscous material, i.e., intermediate trimethylolpropane core, amino terminated dendrimer (TMPTA-HDA-9NH for abbreviation).

37.52 g of phosphorous acid (99.0%, 0.453 mol) and 54.26 g of concentrated hydrochloric acid (37%, 0.550 mol) were respectively placed and uniformly mixed in a four-necked flask equipped with a condenser, a stirring, a thermometer and a dropping funnel. Next, 47.60 g (50%, 0.05 mol) aqueous solution of the intermediate trimethylolpropane core, amino terminated dendrimer (TMPTA-EDA-9NH) was slowly added to above mixture solution with cooling and stirring in such a rate to maintain temperature below 40° C. The resulting mixture was heated up to 85° C., and 44.60 g of formaldehyde solution (37%, 0.550 mol) was then added to the mixture with stirring to form a reaction mixture. The temperature of the reaction mixture maintained at 90° C. for 1 hour, and then was elevated to 104° C. for a reflux period of 4 hours. After the reflux, reaction mixture was concentrated at 104° C. for 1 hour, and meanwhile, hydrochloric acid was removed off with HCl absorption bottle. Next, the reaction mixture was cooled to ambient temperature, to give an amber transparent liquid product with 39.29% solid content by weight, i.e., the trimethylolpropane core, phosphonic acid terminated dendrimer (TMPTA-HDA-9PO$_3$H$_2$).

$^{13}$C NMR (D$_2$O) of TMPTA-HDA-9NH: 6.98; 20.01; 25.11; 25.85; 29.26; 30.08; 36.27; 36.88; 41.21; 47.94; 48.82; 67.43; 172.36 ppm.

$^{13}$C NMR (D$_2$O) of TMPTA-HDA-9PO$_3$H$_2$: 8.01; 21.19; 28.21; 28.81; 29.73; 29.98; 34.66; 36.43; 52.32; 52.93; 53.37; 58.23; 59.77; 66.34; 176.52 ppm.

Example 5

Inhibition Scale Efficiency Test

The static testes for the inhibition efficiency of the antiscalants according to the examples 1~4 on calcium carbonate, calcium sulfate and barium sulfate scale precipitation were performed as following methods.

Static inhibition efficiency test for calcium carbonate was performed by referring to national standard of the People's Republic of China, calcium carbonate deposition method for testing scale inhibiting efficiency of water treatment agent (GB/T 16632-2008). 500 mL of test solution containing 10 mg·L$^{-1}$ of antiscalant (dry basis), 240 mg·L$^{-1}$ of Ca$^{2+}$ and 732 mg·L$^{-1}$ of HCO$_3^-$ was prepared by adding calculated volume antiscalant stock solution, calcium stock solution, bicarbonate stock solution and double distilled water, respectively, to a glass bottle. The pH of each test solution was adjusted to 9.0 by using borate buffer Solution. The bottles were incubated in a water bath for 18 hour at 80° C. After cooling, an aliquot quantity was filtered through 0.22 µm filter paper, and then the calcium concentration in the filtrate was measured using the standard EDTA titration method. Meanwhile, the control test in the absence of antiscalant was conducted.

Static inhibition efficiency test for calcium sulfate was performed similar to the static calcium carbonate inhibition efficiency. The 500 mL of test solution contained 5 mg·L$^{-1}$ of antiscalant (dry basis), 2500 mg·L$^{-1}$ of Ca$^{2+}$ and 7500 mg·L$^{-1}$ of SO$_4^{2-}$. It was adjusted to 7.00±0.1 by the addition of HCl and/or NaOH solution (10%). The bottles were incubated in a water bath for 18 hour at 80° C. After cooling, an aliquot quantity was filtered through 0.22 µm filter paper, and then the calcium concentration in the filtrate was measured by using the standard EDTA titration method. Meanwhile, the control test in the absence of antiscalant was conducted.

Static inhibition efficiency test for barium sulfate was performed as follows. 500 mL of test solution containing 5 mg·L$^{-1}$ of antiscalant (dry basis), 20 mg·L$^{-1}$ of Ba$^{2+}$ and 100 mg·L$^{-1}$ of SO$_4^{2-}$ was prepared by adding calculated volume antiscalant stock solution, barium stock solution, sulfate stock solution and double distilled water, respectively, to a glass bottle. The pH of each test solution was adjusted to 7.0 by using borate buffer Solution. The bottles were incubated in a water bath for 16 hours at 65° C. After cooling, an aliquot quantity was filtered through 0.22 nm filter paper, and then the Ba$^{2+}$ concentration in the filtrate was measured by using the atomic emission spectrometry method. Meanwhile, the control test in the absence of antiscalant was conducted.

The inhibition scale efficiency of the antiscalant is calculated by:

$$\text{Inhibition (\%)} = [(C_i - C_{control})/(C_0 - C_{control})] \times 100\%$$

Where: $C_i$ is the calcium or barium concentration of the sample with the addition of the polymeric inhibitor after incubation, $C_{control}$ is the calcium or barium concentration of the sample with the addition of the antiscalant before incubation, $C_0$ is the calcium or barium concentration of the sample without of the addition of the antiscalant after incubation.

TABLE 1

Result of inhibition scale efficiency test

| Ex. No. | Antiscalants | Inhibition efficiency for CaCO$_3$ (%) | Inhibition efficiency for CaSO$_4$ (%) | Inhibition efficiency for BaSO$_4$ (%) |
|---|---|---|---|---|
| Example 1 | TMPTA-EDA-9PO$_3$H$_2$ | 85.92 | 94.29 | 98.57 |
| Example 2 | TMPTA-PDA-9PO$_3$H$_2$ | 84.01 | 94.46 | 97.03 |
| Example 3 | TMPTA-BDA-9PO$_3$H$_2$ | 84.02 | 94.39 | 96.99 |
| Example 4 | TMPTA-HDA-9PO$_3$H$_2$ | 82.25 | 95.08 | 93.56 |
| Comparison example 1 | ATMP | 54.21 | 72.19 | 80.23 |
| Comparison example 2 | EDTMP | 57.81 | 77.23 | 87.79 |
| Comparison example 3 | HTDMP | 65.77 | 81.14 | 84.23 |
| Comparison example 4 | PAPEMP | 74.57 | 90.32 | 51.23 |

Table 1 summarizes static inhibition scale efficiency tests for the trimethylolpropane core, phosphonic acid terminated dendrimer as well as several prior art antiscalants. The inhibition efficiency on CaCO$_3$, CaSO$_4$ and BaSO$_4$ of the trimethylolpropane core, phosphonic acid terminated dendrimer is far better than micromolecular phosphonate antiscalants ATMP, EDTMP and HTDMP in comparison examples 1~3. The inhibition efficiency on CaCO$_3$, CaSO$_4$ thereof is slightly better than macromolecular oligomer phosphonate PAPEMP in comparison example 4, but the inhibition efficiency on BaSO$_4$ is far better than PAPEMP.

Example 6

The Effect of the Antiscalant Concentration on the Inhibition Calcium Carbonate Scale Efficiency The 500 mL of test solution containing a certain concentration of antiscalant, 200 mg·L$^{-1}$ of Ca$^{2+}$ (500 mg·L$^{-1}$ as CaCO$_3$) and 732 mg·L$^{-1}$ of HCO$_3^-$ was prepared by adding calculated volume antiscalant stock solution, calcium stock solution, bicarbonate stock solution and double distilled water, respectively, to a glass bottle. The pH of each test solution is adjusted to 9.0 by using borate buffer Solution. The bottles were incubated in a water bath for 10 hour at 80° C. After cooling, an aliquot quantity was filtered through 0.22 µm filter paper, and then the calcium concentration in the filtrate was measured by using the standard EDTA titration method. Meanwhile, the control test in the absence of antiscalant was conducted.

Table 2 summarizes the effect of the antiscalant concentration on the inhibition calcium carbonate scale efficiency. It is shown that micromolecular phosphonate antiscalants exhibit an obvious "threshold effect", meaning that after the dosage of phosphonate exceeds a certain value (12 mg·L$^{-1}$ for PBTCA, 8 mg·L$^{-1}$ for ATMP, 10 mg·L$^{-1}$ for EDTMP, and 14 mg·L$^{-1}$ for HTDMP) the inhibition efficiency is not enhanced, but will decrease by further phosphonate concentration increase. However, the inhibition efficiency of the trimethylolpropane core, phosphonic acid terminated dendrimer prepared in the present invention improves with the increase of its concentration in the range of experimental concentrations. When its concentration exceeds 6 mg·L$^{-1}$, the inhibition scale efficiency thereof is better than all of the micromolecular phosphonate antiscalants in the comparison examples 1~3. The trimethylolpropane core, phosphonic acid terminated dendrimer is able to inhibit the formation of calcium carbonate completely, and is better than the oligomer phosphonate PAPEMP in comparison example 4.

TABLE 2

The effect of antiscalant concentrations on the inhibition CaCO$_3$ efficiency

| Ex. No. | Antiscalants | Inhibition efficiency for CaCO$_3$ (%) Antiscalant Concentration (mg · L$^{-1}$) | | | | | | | |
|---|---|---|---|---|---|---|---|---|---|
| | | 2 | 4 | 6 | 8 | 10 | 12 | 14 | 16 |
| Example 1 | TMPTA-EDA-9PO$_3$H$_2$ | 48.22 | 61.91 | 75.02 | 89.79 | 94.55 | 99.22 | 100 | 100 |
| Example 2 | TMPTA-PDA-9PO$_3$H$_2$ | 45.53 | 55.98 | 71.09 | 85.92 | 92.35 | 97.82 | 99.01 | 100 |
| Example 3 | TMPTA-BDA-9PO$_3$H$_2$ | 43.88 | 55.14 | 70.31 | 83.29 | 91.27 | 96.65 | 98.22 | 100 |
| Example 4 | TMPTA-HDA-9PO$_3$H$_2$ | 40.03 | 53.26 | 65.21 | 78.53 | 89.23 | 93.91 | 98.22 | 100 |
| Comparison example 1 | ATMP | 50.55 | 60.18 | 69.54 | 73.89 | 72.31 | 70.99 | 70.17 | 70.15 |
| Comparison example 2 | EDTMP | 48.11 | 56.32 | 66.84 | 73.83 | 80.58 | 79.45 | 78.23 | 77.22 |
| Comparison example 3 | HTDMP | 42.88 | 54.43 | 61.84 | 70.86 | 82.62 | 85.75 | 86.22 | 87.58 |
| Comparison example 4 | PAPEMP | 30.64 | 46.33 | 64.11 | 77.22 | 84.24 | 90.22 | 95.32 | 100 |

Example 7

The Inhibition Scale Efficiency Under the Condition of High Calcium Concentration The 500 mL of test solution containing a certain concentration of antiscalant, 600 mg·L$^{-1}$ of Ca$^{2+}$ (1500 mg·L$^{-1}$ as CaCO$_3$) and 750 mg·L$^{-1}$ of HCO$_3^-$ was prepared by adding calculated volume antiscalant stock solution, calcium stock solution, bicarbonate stock solution and double distilled water, respectively, to a glass bottle. The pH of each test solution is adjusted to 9.0 by using borate buffer Solution. The bottles were incubated in a water bath for 10 hour at 80° C. After cooling, an aliquot quantity was filtered through 0.22 μm filter paper, and then the calcium concentration in the filtrate was measured by using the standard EDTA titration method. Meanwhile, the control test in the absence of antiscalant was conducted.

Table 3 summarizes the effect of the antiscalant concentration on the inhibition calcium carbonate scale efficiency under the condition of high calcium concentration.

It is shown that the trimethylolpropane core, phosphonic acid terminated dendrimer in the present invention has an excellent scale inhibiting efficiency under the condition of high calcium concentration. With the increasing of the dosage of the antisalants, micromolecular phosphonate antiscalants in comparison examples 1~3 combine easily with the higher concentration calcium ions to form Ca-phosphonate precipitates, which causes the sharp decreasing of the inhibiting scale efficiency. However, the trimethylolpropane core, phosphonic acid terminated dendrimer in the present invention can still remain a high scale inhibiting rate, and is better than the oligomer phosphosnate PAPEMP in comparison example 4.

TABLE 3

The effect of antiscalant concentrations on the inhibition calcium carbonate efficiency under the high calcium concentration

| Ex. No. | Antiscalants | Inhibition efficiency for CaCO$_3$ (%) Antiscalant Concentration (mg · L$^{-1}$) | | | | |
|---|---|---|---|---|---|---|
| | | 5 | 10 | 20 | 30 | 40 |
| Example 1 | TMPTA-EDA-9PO$_3$H$_2$ | 52.33 | 74.63 | 82.47 | 85.32 | 88.32 |
| Example 2 | TMPTA-PDA-9PO$_3$H$_2$ | 51.04 | 73.35 | 81.09 | 87.09 | 90.01 |
| Example 3 | TMPTA-BDA-9PO$_3$H$_2$ | 50.92 | 73.02 | 82.62 | 86.82 | 91.18 |
| Example 4 | TMPTA-HDA-9PO$_3$H$_2$ | 48.21 | 71.29 | 84.08 | 89.31 | 92.37 |
| Comparison example 1 | ATMP | 15.06 | 21.92 | 30.4 | 20.33 | 18.22 |
| Comparison example 2 | EDTMP | 17.21 | 30.89 | 40.99 | 31.99 | 24.38 |
| Comparison example 3 | HTDMP | 16.9 | 40.36 | 55.06 | 45.06 | 40.19 |
| Comparison example 4 | PAPEMP | 15.33 | 44.11 | 66.22 | 77.44 | 80.1 |

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A trimethylolpropane core, phosphonic acid terminated dendrimer comprising a formula illustrated as follows:

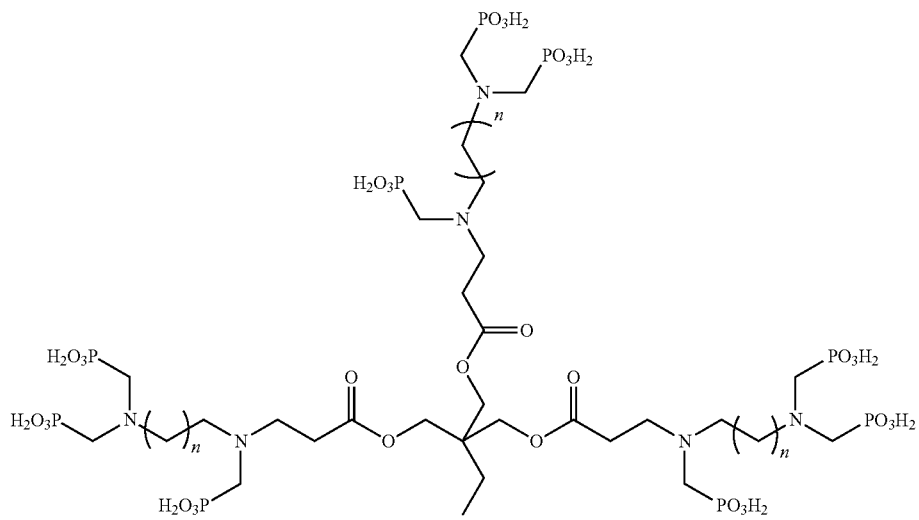

wherein n is an integer from 1 to 5.

2. The trimethylolpropane core, phosphonic acid terminated dendrimer, as recited in claim 1, wherein the trimethylolpropane core, phosphonic acid terminated dendrimer is prepared by the steps of: (1) processing a Michael reaction on trimethylolpropane triacrylate and alkylidene diamine, comprising adding the alkylidene diamine into a round-bottom flask equipped for stirring and having a reflux condenser and a thermometer, cooling to below 10° C. under nitrogen, adding a methanol solution of the trimethylolpropane triacrylate to the round-bottom flask to obtain a mixture, allowing the mixture to react at 25-35° C. for 20-48 hours to obtain a result solution, subjecting the result solution to vacuum distillation to remove excess alkylidene diamine and methanol at 60-110° C. for 5 to 10 hours to obtain an intermediate trimethylolpropane core, amino terminated dendrimer, wherein a general reaction equation thereof is as follows:

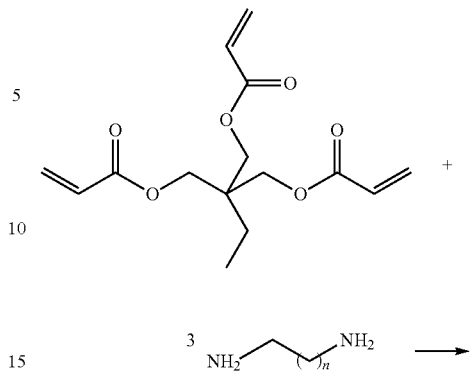

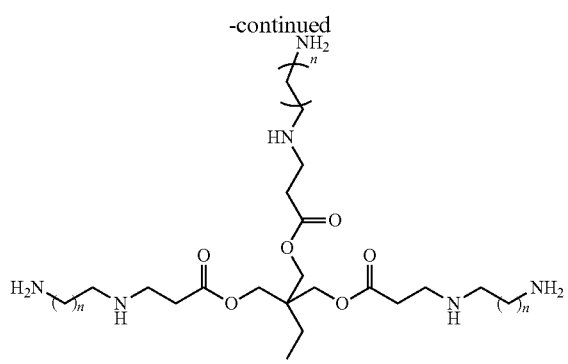

wherein n is an integer from 1 to 5, and (2) processing a methylene phosphonation reaction on the intermediate, trimethylolpropane core, amino terminated dendrimer, comprising placing phosphorous acid and concentrated hydrochloric acid in a four-necked flask equipped for stirring and having a condenser, a thermometer, and a dropping funnel, adding an aqueous solution of the intermediate, trimethylolpropane core, amino terminated dendrimer to a mixture solution of the phosphorous acid and the concentrated hydrochloric acid with cooling and stirring to maintain a temperature below 40° C. to obtain a resulting mixture; heating the reaction mixture to 85-90° C. and adding a formaldehyde solution to the resulting mixture with stirring to form a reaction mixture, maintaining the temperature of the reaction mixture at 90° C. for 1-2 hours, raising the temperature to 102-105° C. for a reflux period; after the reflux period, concentrating the reaction mixture at 102-105° C. while removing hydrochloric acid with an HCl adsorption bottle, and cooling the reaction mixture to ambient temperature to obtain the trimethylolpropane core, phosphonic acid terminated dendrimer, wherein a general reaction equation thereof is as follows:

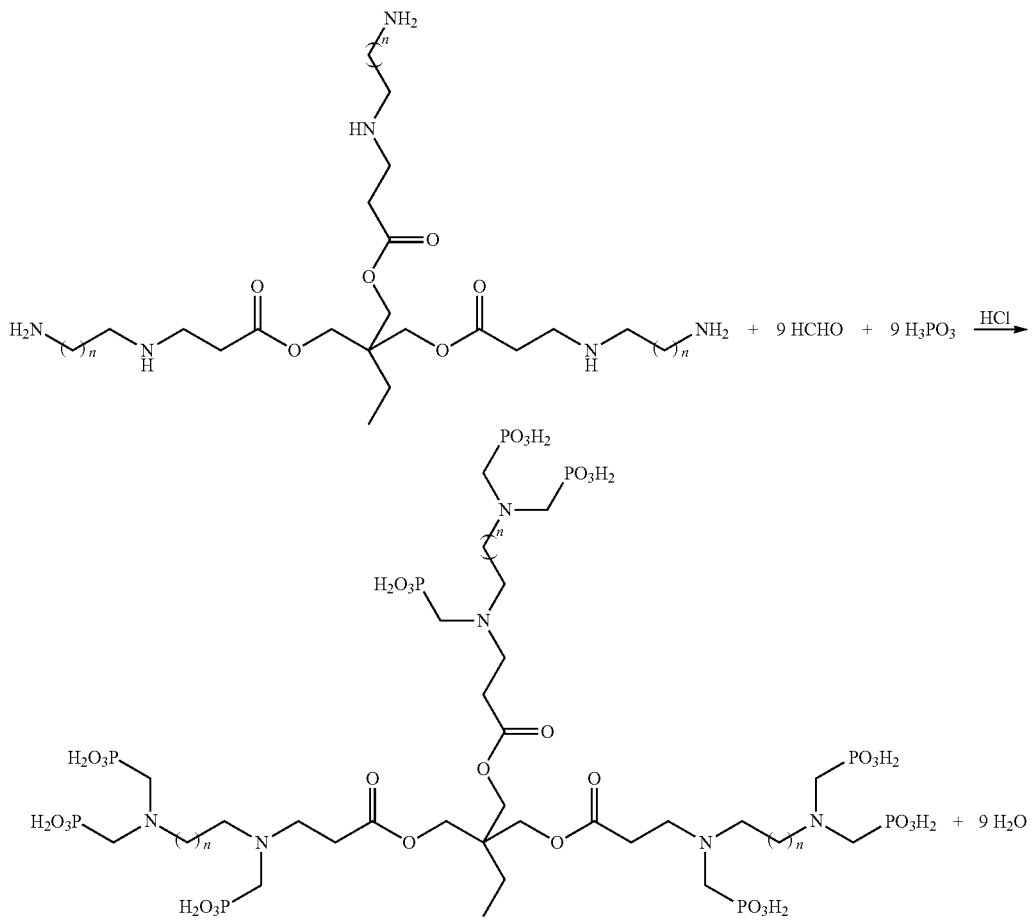

wherein n is an integer from 1 to 5.

3. The trimethylolpropane core phosphonic acid terminated dendrimer, as recited in claim 2, wherein in the Michael reaction of the step (1), a molar ratio of the trimethylolpropane triacrylate to the alkylidene diamine is 1:(4-6).

4. The trimethylolpropane core, phosphonic acid terminated dendrimer, as recited in claim 2, wherein in the methylene phosphorylation of the step (2), a molar ratio of the intermediate trimethylolpropane core, amino terminated dendrimer, the phosphorous acid, the formaldehyde and the concentrated hydrochloric acid is 1: (9.0-9.2):(11.0-12.0):(11.0-12.0).

5. A method of inhibiting the deposition of scale in water treatment including calcium carbonate, calcium sulfate and barium sulfate, comprising introducing into the water an amount of the trimethylolpropane core, phosphonic acid terminated dendrimer having the formula as recited in claim 1.

6. The method, as recited in claim 5, wherein the water is industrial water including circulating cooling water, oilfield flooding and reverse osmosis.

7. The method, as recited in claim 5, wherein the water has a calcium concentration.

* * * * *